United States Patent [19]

Haber et al.

[11] Patent Number: 4,927,019

[45] Date of Patent: May 22, 1990

[54] COMBINATION NEEDLE SHEATH AND STERILITY PACKAGE

[75] Inventors: Terry M. Haber, El Toro; William H. Smedley, Lake Elsinore; Clark B. Foster, Laguna Niguel; John A. Lewis, Jr., Costa Mesa, all of Calif.

[73] Assignee: Habley Medical Technology Corporation, Laguna Hills, Calif.

[21] Appl. No.: 364,233

[22] Filed: Jun. 12, 1989

[51] Int. Cl.[5] ............................................. B65B 85/24
[52] U.S. Cl. ..................................... 206/365; 206/438
[58] Field of Search ............... 206/365, 366, 364, 571, 206/370, 438

[56] References Cited

U.S. PATENT DOCUMENTS

| | | | |
|---|---|---|---|
| 2,677,373 | 5/1954 | Barradas | 206/365 |
| 3,294,089 | 12/1966 | Brookfield | 206/365 |
| 3,381,813 | 5/1968 | Coanda et al. | 206/365 |
| 3,934,722 | 1/1976 | Goldberg | 206/365 |
| 4,113,090 | 9/1978 | Carstens | 206/365 |

Primary Examiner—Paul T. Sewell
Assistant Examiner—Jacob Ackun, Jr.
Attorney, Agent, or Firm—Morland C. Fischer

[57] ABSTRACT

A combination needle sheath and sterility package comprising a lower needle cover to surround and protect the distal end of a sterile, double ended hypodermic needle cannula and an upper sleeve to surround and protect the proximal end of the cannula. The upper sleeve can be opened to permit the bore of a conventional hypodermic syringe to be received therewithin, so that the proximal end of the needle cannula can communicate fluidically with the syringe cylinder. By virtue of the needle sheath/sterility package as disclosed herein, the sterility of the needle cannula may be reliably preserved during handling and prior to use, while the possibility of an accidental needle stick during attachment of the cannula to the syringe may be advantageously minimized.

20 Claims, 4 Drawing Sheets

COMBINATION NEEDLE SHEATH AND STERILITY PACKAGE

BACKGROUND OF THE INVENTION

1. Field of the Invention

This invention relates to a combination needle sheath and sterility package to surround and protect a sterile, double ended needle cannula which is to be attached in fluid communication to a hypodermic syringe, whereby the sterility of the cannula can be preserved and the possibility of an accidental needle stick minimized.

2. Background Art

It is well known to package a double ended needle cannula in a suitable container which surrounds and protects the cannula during transport and storage. Just prior to use, the cannula is removed from the package to be interfaced with a hypodermic syringe. It is common to surround the distal end of the double ended cannula with a needle cover to maintain the sterility tehreof and prevent an accidental needle stick while the cannula is being attached to the syringe. However, it is also common to unsheath and, thereby, expose the proximal end of the cannula so as to enable said proximal end to be moved into fluid communication with the cylinder of the syringe.

With the proximal end of the needle cannula exposed, the sterility thereof may be jeopardized. Moreover, a health care worker may accidentally stick himself with the exposed proximal end due to a careless handling of the cannula or an unsuccessful attempt to attach the cannular to a syringe. Such an accidental needle stick could contaminate the cannula and thereby, spread a contageous and possibly life threatening disease to an unsuspecting patient.

Accordingly, it would be desirable to be able to reliably protect and shield both the proximal and distal ends of a double ended needle cannula by means of a package that is adapted to preserve the sterility of the cannula and, at the same time, avoid an accidental needle stick during transport, handling, and attachment of the cannula to the syringe.

SUMMARY OF THE INVENTION

In general terms, a combination needle sheath and sterility package is disclosed to surround and protect the proximal and distal ends of a sterile, double ended needle cannula. The cannula is carried by a screw threaded hub that is to be attached to the cylinder of a conventional hypodermic syringe. By virtue of the needle sheath/sterility package, the sterility of the cannula can be reliable preserved and an accidental needle stick avoided during handling and while the hub is being attached to the syringe cylinder. According to a first embodiment of the invention, the needle sheath/sterility package comprises a lower needle cover to surround and protect the distal end of the cannula and an upper telescope sleeve to surround and protect the proximal end of the cannula. The upper telescoping sleeve is adapted to slide over the lower needle cover. The upper sleeve has an open proximal end which is covered, in the as-packaged configuration, by a tear-off strip or by a detachable end cap. With the proximal end of the upper sleeve opened, a syringe cylinder may be moved therethrough and into mating engagement with the needle carrying hub. At the same time that the hub is mated to the cylinder, the telescope upper sleeve slides axially and distally over the lower needle cover. The needle sheath/sterility package is then removed leaving the proximal end of the cannula in fluid communication with the cylinder and the distal end of the cannula exposed for penetrating the skin of a patient.

According to a second embodiment, the needle sheath/sterility package is characterized by a one-piece construction including a lower needle cover to surround and protect the distal end of the cannula and an upper sleeve coextensively connected to the lower needle cover to surround and protect the proximal end of the cannula. The needle carrying hub has a hexagonal base that is sized to be received within a corresponding hexagonal receptacle of the upper sleeve. A rotational force applied to the upper sleeve is transferred first to the receptacle thereof and then to the hub which is located within said receptacle. In this manner, the needle carrying hub can be reliably rotated into engagement with the syringe cylinder with the proximal end of the cannula moved into fluid communication with said cylinder.

According to a third embodiment, the sleeve of the needle sheath/sterility package includes a pair of semi-cylindrical sleeve sections. Each of the sleeve section rotates outwardly and around a respective hinge when the syringe cylinder is received through the open proximal end of the upper sleeve so that the needle carrying hub can be rotated into engagement with the syringe.

In a fourth embodiment, the upper sleeve of the needle sheath/sterility package includes a bellows that is compressible from an expanded state to a collapsed state. In the as-packaged configuration, the bellows assumes the expanded state to surround and protect the proximal end of the cannula. As the syringe cylinder is received through the open proximal end of the upper sleeve, the bellows is compressed to the collapsed state to permit the needle carrying hub to be rotated into engagement with the syringe and the proximal end of the cannula to be moved into fluid communication with the syringe cylinder.

DESCRIPTION OF THE PREFERRED EMBODIMENT

The combination needle sheaths and sterility packages which form the present invention are best described while referring to the drawings. As will soon be described, each needle sheath and sterility package disclosed herein is adapted to surround and protect the distal and proximal ends of a sterile, double ended hypodermic needle cannula of the type that is to be attached to a conventional hypodermic syringe in fluid communication with the cylinder or barrel thereof so that a fluid can be expulsed (or infused) from the cylinder via the cannula. In this manner, not only will the sterility of the cannula be preserved prior to use, but the possibility of an accidental needle stick during handling and attachment of the cannula to the syringe can be advantageously minimized.

Figure 3:
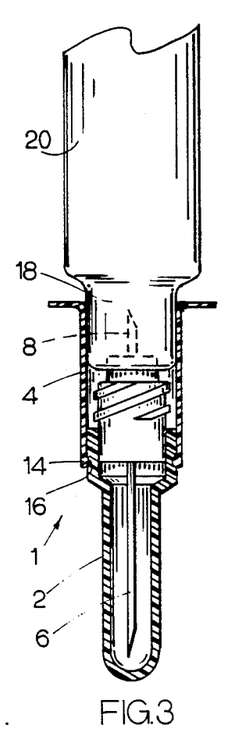
FIG. 3 shows a cross-section of the needle sheath/-sterility package being attached to the cylinder of a hypodermic syringe.

According to a first embodiment of the invention, and referring to FIGS. 1-4 of the drawings, a combination needle sheath and sterility package 1 is illustrated and characterized by a lower needle cover 2 and an upper telescoping sleeve 4. As shown in the as-packaged configuration of FIGS. 1 and 2, the needle cover 2 surrounds and protects the distal end 6 of a sterile, double ended needle cannula. The upper sleeve 4 surrounds and protects the proximal end of the cannular and is coaxially aligned with the lower needle cover 2 so as to be slidable thereover. The needle cannula is carried by a screw threaded hub 9 which is adapted to be mated to the cylinder of the hypodermic syringe. The upper sleeve 4 has an open proximal end within which the distal bore (designated 18 in FIG. 3) of the syringe cylinder 20 can be received when mating the hub 9 to the syringe. A sealing flange 10 extends around the periphery of the open proximal end of upper sleeve 4. A sterile paper seal 12 having a tear-off tab 13 is removably affixed to the sealing flange 10 to prevent contamination and loss of sterility to the cannula by sealing the proximal end of upper sleeve 4 from the atmosphere until such time that it is desirable to mate the cannula carrying hub 9 to the syringe cylinder 20. In FIG. 3 of the drawings, the sterile seal 12 has been removed (i.e. pulled off) from the needle sheath/sterility package 1 to open the proximal end of outer sleeve 4 for receipt of the distal bore 10 of syringe cylinder 20. The upper telescoping sleeve 4 has a peripheral locking ring 14 projecting radially inward therefrom. Locking ring 14 is received (in the as-packaged configuration) within a groove 16 that is formed around the periphery of lower needle cover 2. In this manner, the needle cover 2 and telescoping sleeve 4 of needle sheath/sterility package 1 are retained in axial alignment with one another so as to completely surround and safely shield the distal and proximal ends 6 and 8 of the needle cannula and thereby prevent an accidental needle stick during handling and attaching of the cannula to the syringe.

That is, with the distal and proximal ends 6 and 8 of the cannula still surrounded and shielded by the lower needle cover 2 and upper sleeve 4 of needle sheat/sterility package 1, the distal bore 18 of the syringe cylinder 20 is moved through the open proximal end of upper sleeve 4. It is preferable that the adjacent walls of upper sleeve 4 and bore 18 form a secure friction fit so that the proximal end 18 of the cannula can be automatically and properly aligned for receipt through bore 18 and fluid communication with cylinder 20.

Figure 4:
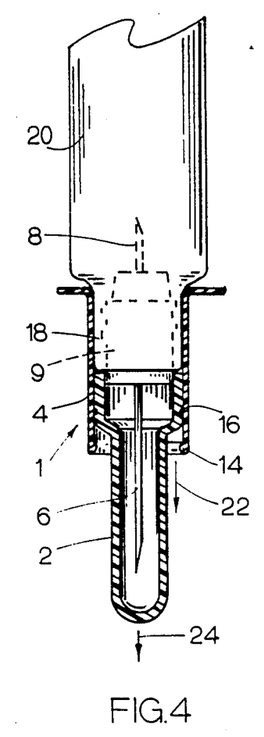
FIG. 4 shows the cross-section of FIG. 3 with the needle sheath/sterility package attached to the cylinder of a syringe.

As is shown in FIG. 4 of the drawings, the telescoping upper sleeve 2 of needle sheath/sterility package 1 is moved axially and distally over the lower needle cover 2 so that the screw threaded needle hub 9 can be mated to the cylinder 20 at corresponding screw threads (not shown) formed around the distal bore 18. More particularly, by applying a distal pulling force (indicated by the direction of reference arrow 22) to upper sleeve 4, the locking ring 14 is moved out of contact with the groove 16 of lower needle cover 2 to permit a displacement of the telescoping upper sleeve relative to the lower needle cover. The amount of displacement of upper sleeve 4 over lower needle cover 2 during the attachment of 9 to cylinder 20 is dependent upon the length of the cylinder bore 18, such that needle sheath/sterility package 1 will be adapted to fix bores of different sizes. Once the hub 9 has been suitably attached to the syringe to move the proximal end 8 of the needle cannula into fluid communication with cylinder 20, the needle sheath/sterility package 1 may be removed from the cannula by grasping the lower needle cover 2 and applying a distal pulling force thereto (indicated by the direction of reference arrow 24). Hence, the distal end 6 of the cannula will now be exposed to penetrate the tissue of a patient.

Figure 1:
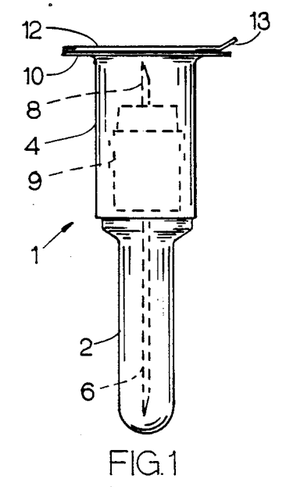
FIG. 1 shows a front view of a combination needle sheath and sterility package in the as-packaged configuration according to a first embodiment of the present invention.
Figure 2:
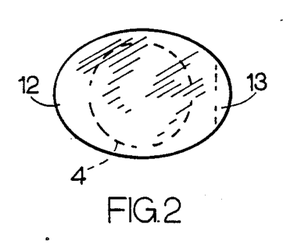
FIG. 2 is an end view of the needle sheath/sterility package of FIG. 1.
Figure 5:
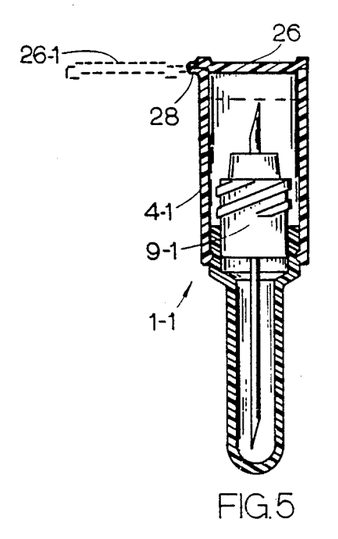
FIG. 5 is a cross-section of the needle sheath/sterility package having an optional rotatable end cap.
Figure 6:
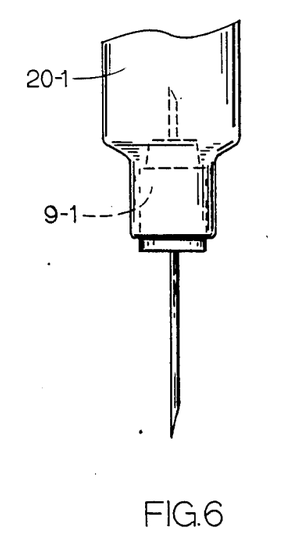
FIG. 6 shows a syringe cylinder and a double ended needle cannula connected thereto with the needle sheath/sterility package removed so that an injection may be administered.
Figure 7:
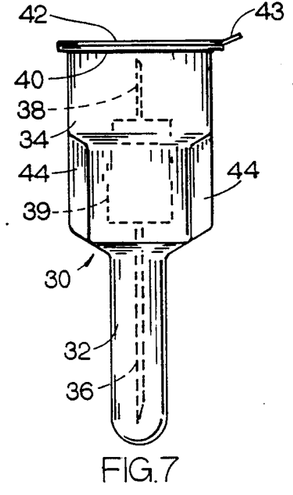
FIG. 7 illustrates a combination needle sheath and sterility package in the as-packaged configuration according to a second embodiment of the invention.
Figure 8:
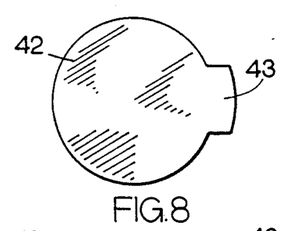
FIG. 8 is an end view of the needle sheath/sterility package of FIG. 7.

FIGS. 5 and 6 of the drawings show a modification of the combination needle sheath and sterility package 1 of FIGS. 1-4. More particularly, the peripheral sealing flange 10 and paper seal 12 of FIG. 1 are replaced in the needle sheath/sterility package 1-1 of FIGS. 5 and 6 by a plastic end cap 26. In the as-packaged configuration of FIG. 5, cap 26 is pivotally connected across the proximal end of outer sleeve 4-1 by means of a hinge 28.

Thus, instead of tearing off the paper seal 12 of FIG. 1, access to the interior of upper telescope sleeve 4-1 is available by rotating end cap 26 around its hinge 28 from the closed position (as illustrated) to the open position (shown in phantom and designated by the reference numberal 26-1). The rotatable end cap 26 is removable along with the needle sheath/sterility package 1-1 after the needle hub 9-1 has been suitably attached to the syringe cylinder 20-1, such that the needle cannula communicates fluidically with the cylinder to permit an injection to be administered (best shown in FIG. 6).

FIGS. 7-12 of the drawings illustrate a combination needle sheath and sterility package 30 according to a second embodiment of the invention. As shown in the as-packaged configuration of FIGS. 7 and 8, the needle sheath/sterility package 30 is characterized by a one piece construction comprising a lower needle cover 32 to surround and protect the distal end 36 of a sterile, double ended needle cannula and an upper sleeve 34 coextensively connected to the lower needle cover 32 to surround and protect the proximal end 38 of the cannula. The cannula is carried by a screw threaded hub 39 which is adapted to be mated to the cylinder of a hypodermic syringe. The upper sleeve 34 has an open proximal end through which the distal bore (designated 48 of FIG. 9) of the syringe cylinder 50 can be received when mating the hub 39 to the cylinder. A sealing flange 40 extends around the periphery of the open proximal end of upper sleeve 34. A sterile paper seal 42 having a tear-off tab 43 is affixed to sealing flange 40 to prevent contamination of the cannula and loss of sterility by sealing the proximal end of sleeve 4 from the atmosphere until such time as when it is desirable to mate the cannula carrying hub 39 to the syringe cylinder 50. A pair of axially extending finger wings 44 project outwardly from opposite sides of upper sleeve 34 for a purpose that will be described in greater detail when referring to FIG. 10.

Figure 9:
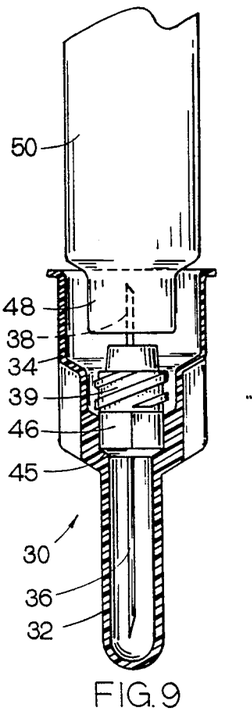
FIG. 9 shows a cross-section of the needle sheath/-sterility package and an associated double ended needle cannula being attached to the cylinder of a syringe.

In FIG. 9 of the drawings, the sterile seal 42 has been removed (i.e. pulled off) from the needle sheath/sterility package 30 to open the proximal end of upper sleeve 34 for receipt of the distal bore 48 of the syringe cylinder 50. The upper sleeve 34 includes, at its intersection with lower needle cover 32, a receptacle 45 having a generally hexagonal cross-section (best shown in FIG. 11). The needle carrying hub 39 includes a base 46 which also has a generally hexagonal cross-section (also best shown in FIG. 11). In the as-packaged configuration, the hexagonal base 46 of hub 39 is received within the hexagonal receptacle 45 of upper sleeve 34. In this manner, the lower needle cover 32 and upper sleeve 34 of the needle sheath/sterility package 30 completely surround and safely shield the distal and proximal ends 36 and 38 of the needle cannula while aligning the cannula for fluid communication with the cylinder 50.

Figure 10:
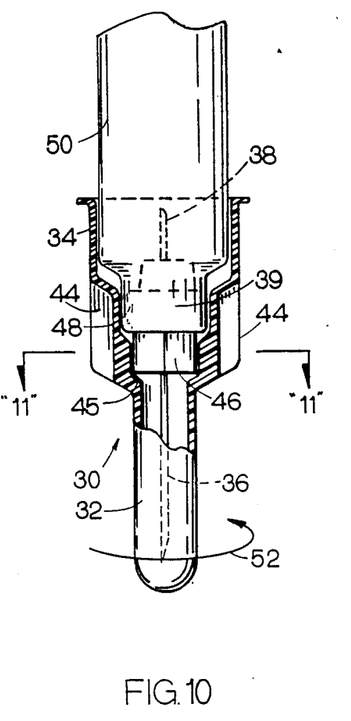
FIG. 10 shows the needle sheath/sterility package and needle cannula of FIG. 9 attached to the syringe cylinder.
Figure 11:
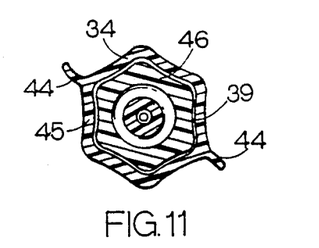
FIG. 11 is a cross-section taken along lines 11—11 of FIG. 10.
Figure 12:
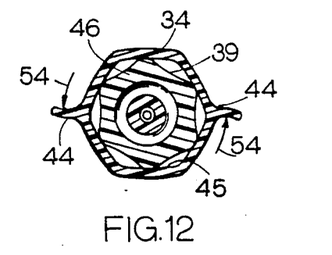
FIG. 12 shows the cross-section of FIG. 11 with the needle sheath/sterility package being rotated relative to a needle carrying hub.

Referring concurrently to FIGS. 10-12 of the drawings, the distal bore 48 of syringe cylinder 50 is shown after being moved through the open proximal end of the upper sleeve 34 of needle sheath/sterility package 30, whereby the proximal end 38 of the needle cannula is moved into fluid communication with said cylinder 50. More particularly, a rotational force applied to upper sleeve 34 (in the direction of reference arrow 52) at the finger wings 44 thereof is transferred to the hexagonal receptacle 45 of upper sleeve 34. Inasmuch as the hexagonal base 46 of needle hub 39 is received within the hexagonal receptacle 45, a rotation of the upper sleeve 34 causes a corresponding rotation of the hub 39. Accordingly, the screw threaded hub 39 will be rotated into mating engagement with the screw threaded bore 38 of cylinder 50 with the lower needle cover 32 and upper sleeve 34 still surrounding and protecting the distal and proximal ends 36 and 38 of the needle cannula.

Referring particularly to FIG. 12, after the needle carrying hub 39 has been rotated into mating engagement with the syringe cylinder, any further rotation of the upper sleeve 34 (in the direction of reference arrows 54) at the finger wings 44 will cause the hexagonal receptacle 45 of sleeve 34 to be rotated relative to the hexagonal base 46 of hub 39. That is, the corners of receptacle 45 are rotated out of receipt of corresponding corners of hub base 46 and into receipt of immediately adjacent corners of said base. The foregoing "one-click" rotation of upper sleeve 34 relative to hub 39 creates a positive snap-lock which prevents any further rotation of said upper sleeve 34 in response to a rotational force or torque applied at finger wings 44 and assures that needle carrying hub 39 is reliably mated to distal bore 48 with the needle cannula properly moved into fluid communication with syringe cylinder 50.

Figure 13:
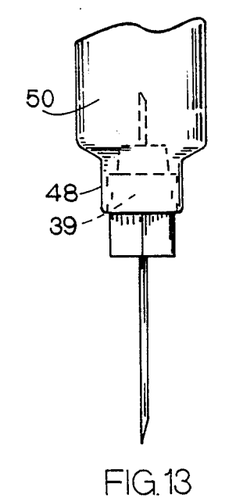
FIG. 13 shows the needle cannular connected to the cylinder of the syringe with the needle sheath/sterility package removed therefrom so that an injection can be administered.

FIG. 13 of the drawings shows the double ended needle cannula carried by hub 39 attached to the distal bore 48 of cylinder 50 with the aforementioned needle sheath/sterility package 30 removed therefrom so that an injection may be administered in a medically acceptable fashion.

FIGS. 14-17 of the drawings illustrate a combination needle sheath and sterility package 60 according to a third embodiment of the invention. As shown in the as-packaged configuration of FIGS. 14 and 15, needle sheath/sterility package 60 comprises a lower needle cover 62 to surround and protect the distal end 66 of a sterile, double ended needle cannula and an upper sleeve 64 coextensively connected to the lower needle cover 62 to surround and protect the proximal end 68 of the needle cannula. The cannula is carried by a screw threaded hub 69 which is adapted to be mated to the cylinder of a hypodermic syringe. The upper sleeve 64 has an open proximal end through which the distal bore (designated 78 in FIG. 16) of the syringe cylinder 80 can be received when mating the hub 69 to the cylinder. A detachable end cap 70 surrounds the upper sleeve 64 and covers the open proximal end thereof to prevent contamination of the cannula and loss of sterility. Two or more axially extending finger wings 74 project outwardly from the sides of upper sleeve 64 to facilitate the attachment of the needle carrying hub 69 to the syringe cylinder (best described when referring to FIG. 17).

Figure 14:
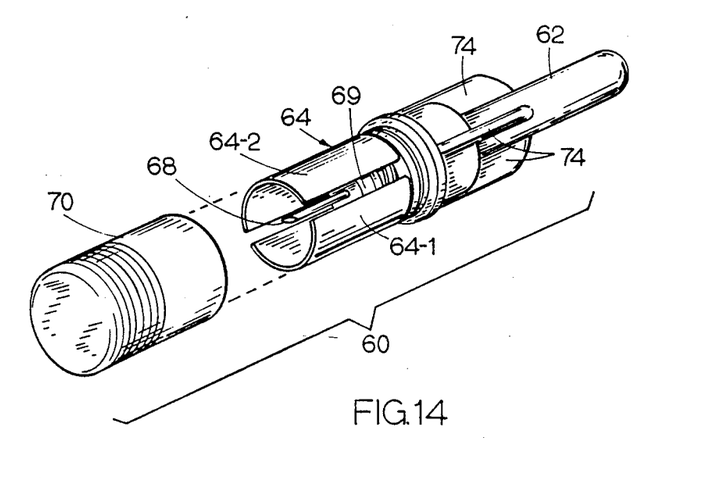
FIG. 14 is an exploded view of a combination needle sheath and sterility package according to a third embodiment of the invention.
Figure 15:
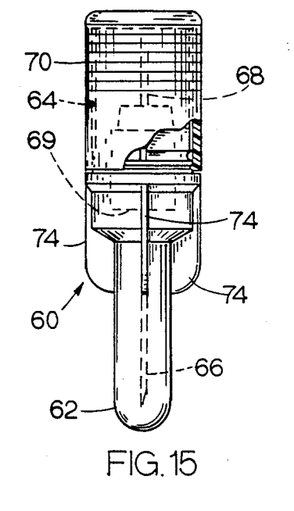
FIG. 15 shows the combination needle sheath and sterility package of FIG. 14 in the as-packaged configuration.

The upper sleeve 64 of the needle sheath/sterility package 60 is characterized by a pair of opposing, semi-cylindrical sleeve members 64-1 and 64-2. Although a pair of sleeve members are shown and described, it is to be understood that upper sleeve 64 may be formed from any suitable number of such members. In the as-packaged configuration, with the end cap 70 surrounding upper sleeve 64, the sleeve member 64-1 and 64-2 are retained in parallel, face-to-face alignment with one another to surround and protect the proximal end 68 of the needle cannula during storage and handling.

Figure 16:
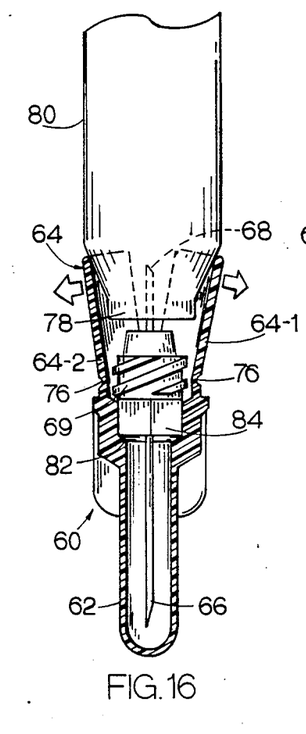
FIG. 16 is a cross-section of the needle sheath/sterility package of FIG. 15 and an associated double ended needle cannula being attached to the cylinder of a hypodermic syringe.

As is best shown in FIG. 16 of the drawings, each of the sleeve members 64-1 and 64-2 is pivotable at a respective hinge 76. That is to say, with the end cap 70 removed from needle sheath/sterility package 60 to open the proximal end of upper sleeve 64, the sleeve members 64-1 and 64-2 can be rotated outwardly around their respective hinges 76 (as indicated by the reference arrows) when the distal bore 78 of a syringe cylinder 80 is received therewithin. In this manner, the lower needle cover 62 and upper sleeve 64 completely surround and safely shield the distal and proximal ends 66 and 68 of the needle cannula during the entire time that the needle carrying hub 69 is being mated to distal bore 78.

Upper sleeve 64 is provided with a hexagonal receptacle 82 for receipt of a corresponding hexagonal base 84 of needle carrying hub 69. With base 84 located in receptacle 82, the proximal end 68 of the needle cannula will be accurately aligned to communicate with the cylinder 80. The torque limiting advantages which are available by means of the hexagonally shaped receptacle 82 and base 84 are similar to those previously described when referring to FIGS. 9-12.

Figure 17:
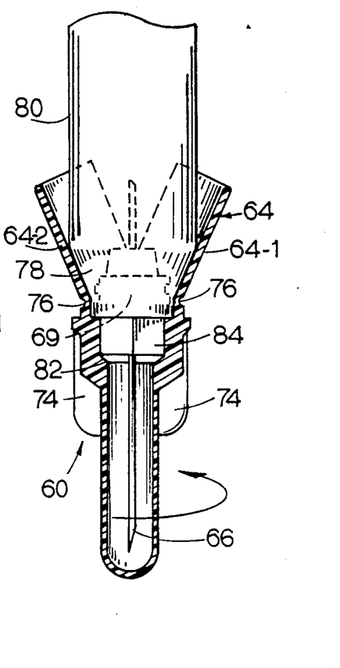
FIG. 17 shows the needle sheath/sterility package and needle cannula of FIG. 16 attached to the syringe cylinder.
Figure 18:
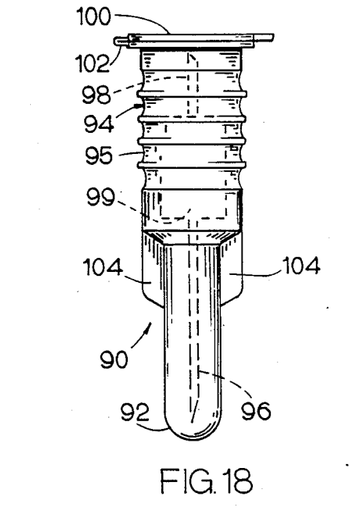
FIG. 18 shows a combination needle sheath and sterility package in the as-packaged configuration according to a fourth embodiment of the invention.
Figure 19:
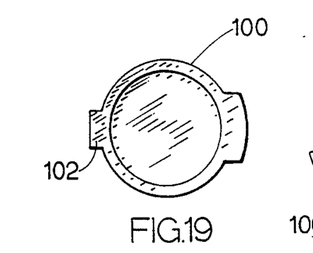
FIG. 19 is an end view of the needle sheath/sterility package of FIG. 18.

In FIG. 17 of the drawings, the distal bore 78 of cylinder 80 is moved completely through the open proximal end of upper sleeve 64 to mate said distal bore to the screw threaded needle carrying hub 69. Hence, the sleeve members 64-1 and 64-2 are spread (i.e. rotated) around their respective hinges 76 to their fully open position to accommodate the distal bore within upper sleeve 64. A rotational force (in the direction of the reference arrow) applied to the finger wings 74 is transferred first to the hexagonal receptacle 82 of upper sleeve 64 and then to the base 84 of needle carrying hub 69 which is received within said receptacle, whereby to rotate the screw threaded hub 69 into reliable mating engagement with the correspondingly screw threaded distal bore 78 of cylinder 80. The needle sheath/sterility package 60 may now be grasped and removed leaving the proximal end 68 of the needle cannula communicating with cylinder 80 of the distal end 66 thereof exposed to penetrate the skin of a patient.

FIGS. 18-21 of the drawings illustrate a combination needle sheath and sterility package according to a fourth embodiment of the invention. As shown in the as-packaged configuration of FIGS. 18 and 19, needle sheath/sterility package 90 comprises a lower needle cover 92 to surround and protect the distal end 96 of a sterile, double ended needle cannula and an upper sleeve 94 coextensively connected to the lower needle cover 92 to surround and protect the proximal end 98 of the cannula. The cannula is carried by a screw threaded hub 99 which is adapted to be mated to the cylinder of a hypodermic syringe. The upper sleeve 94 has an open proximal end through which the distal bore (designated 105 in FIG. 20) of the syringe cylinder 106 can be received when mating the hub 99 to the cylinder. A plastic end cap 100 (similar to the end cap 26 which was previously described when referring to FIG. 5) is pivotally connected across the proximal end of upper sleeve 94 by means of a hinge 102. Access to the interior of outer sleeve 94 is available by rotating cap 100 around hinge 102 from the as-packaged closed position (as illustrated) to an open position (shown in FIG. 20). A pair of axially extending finger wings 104 project radially outward from opposite sides of the upper sleeve 94 to facilitate the attachment of the needle carrying hub 99 to the syringe cylinder.

The upper sleeve 94 of the present embodiment includes an expandable/collapsible bellows 95 that assumes an expanded state in the as-packaged configuration so that the proximal end 98 of the needle cannula may be completely surrounded and shielded during the handling of the needle sheath/sterility package 90 prior to the attachment of needle hub 99 to the syringe cylinder. However, and as will be explained when referring to FIG. 21, the bellows 95 can be forced to a collapsed state during the attachment of needle hub 99 to said cylinder.

Figure 20:
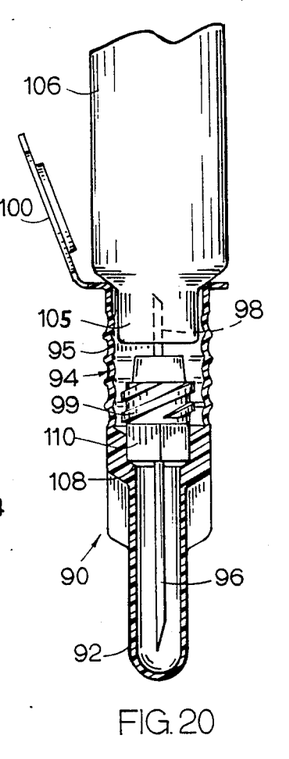
FIG. 20 shows a cross-section of the needle sheath/sterility package of FIG. 18 and an associated double ended needle cannula being attached to the cylinder of a hypodermic syringe.

FIG. 20 of the drawings shows the needle sheath/sterility package 90 after the end cap 100 has been rotated to the open position and the distal bore 105 of syringe cylinder 106 has been received through the open proximal end of upper sleeve 94 so as to be attached to the needle carrying hub 99. The upper sleeve 94 is provided with a hexagonal receptacle 108 for receipt of a corresponding hexagonal base 110 of needle carrying hub 99. With the base 110 located within receptacle 108, the proximal end 98 of the needle cannula will be accurately aligned to communicate with the cylinder 106. The torque limiting advantages which are available by means of a hexagonally shaped receptacle 108 and base 110 are similar to those previously described while referring to FIGS. 9-12.

Figure 21:
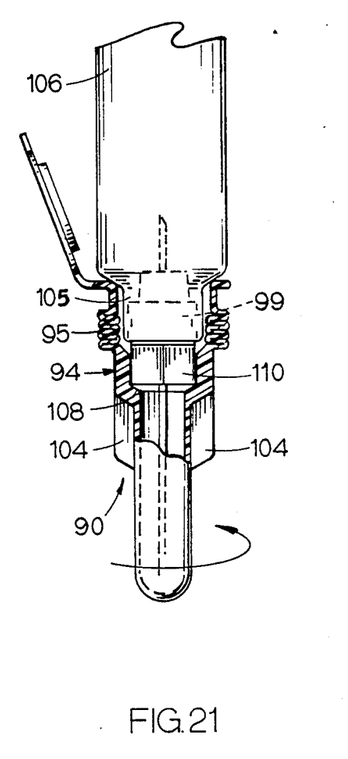
FIG. 21 shows the needle sheath/sterility package and needle cannula of FIG. 20 attached to the syringe cylinder.

Referring now to FIG. 21, the distal bore 105 of cylinder 106 is moved completely through the open proximal end of the upper sleeve 94 to mate the screw threaded needle carrying hub 99 to said distal bore. Accordingly, an axial compressive force is applied to the bellows 95 of the upper sleeve 94 to move said bellows 95 into the collapsed state. A rotational force (in the direction of the reference arrow) applied to finger wings 104 is transferred first to the hexagonal receptacle 108 of upper sleeve 94 and then to the base 110 of needle carrying hub 99 which is received within said receptacle, whereby to rotate said screw threaded hub 99 into reliable mating engagement with the correspondingly screw threaded distal bore 105 of cylinder 106. The needle sheath/sterility package 90 may now be grasped and removed leaving the proximal end 98 of the needle cannula communicating the cylinder 106 and the distal end 96 thereof exposed for penetrating the tissue of a patient.

It will be apparent that while a preferred embodiment of the invention has been shown and described, various modifications and changes may be made without departing from the true spirit and scope of the invention. Having thus set forth the preferred embodiments of the invention, which is claimed is:

1. For a double ended needle cannula to be positioned in fluid communication with the cylinder of a hypodermic syringe and being supported by a needle hub that is adapted to be mated to said cylinder so that the cannula may communicate therewith, a combination needle sheath and sterility package comprising:

first needle cover means detachably connected to the needle hub to surround and protect the distal end of the double ended cannula; and second needle cover means to surround and protect the proximal end of the cannula, said second needle cover means having an open end dimensioned to receive a portion of the syringe cylinder therethrough between the second needle cover means and the needle hub so that the needle hub can be mated to said cylinder with the proximal end of the cannula in fluid communication thereiwth, said second needle cover means being coaxially aligned with and slidable axially over said first needle cover means when the needle hub is mated to the cylinder of the syringe.

2. The combination needle sheath and sterility package recited in claim 1, further comprising closure means removably attached across the open end of said second needle cover means.

3. The combination needle sheath and sterility package received in claim 2, wherein said closure means is a tear-off material covering the open end of said second needle cover means.

4. The combination needle sheath and sterility package recited in claim 2, wherein said closure means is an end cap pivotally connected to said second needle cover means and rotatable from a closed position extending across said open end to an open position at which the needle hub can be mated to the syringe cylinder.

5. The combination needle sheath and sterility package recited in claim 1, further comprising a receptacle having adjacent side walls which are angled relative to one another, said needle hub having adjacent side walls which are also angled relative to one another to correspond with the angle of the side walls of said receptacle, said needle hub being received within said receptacle to align the cannula for communication with the cylinder of the syringe.

6. The combination needle sheath and sterility package recited in claim 5, further comprising at least one outwardly extending finger wing, the application of a rotational force to said finger wing being transferred to the hub via said receptacle to cause said hub to be rotated into mating engagement with the cylinder of the syringe.

7. The combination needle sheath and sterility package recited in claim 1, further comprising releasable retaining means by which to prevent a displacement of said second needle cover means relative to said first needle cover means, said retaining means including a lip formed around the periphery of said second needle cover means and a groove formed around the periphery of said first needle cover means, the releasable receipt of said lip within said groove preventing a displacement of said second needle cover means relative to said first needle cover means.

8. For a double ended needle cannula to be positioned to communicate fluidically with the cylinder of a hypodermic syringe, a combination needle sheath and sterility package comprising a needle cover to surround and protect the distal end of the double ended needle cannula and a sleeve to surround and protect the proximal end iof the cannula, said sleeve having an open end through which a portion of the syringe cylinder can be received so that the needle cannula can be positioned to communicate fluidically with the cylinder while the proximal end of the cannula is surrounded and protected by said sleeve, said sleeve also including at least two generally parallel aligned sleeve sections, first ends of said sleeve sections forming the open end of said sleeve and opposite ends of said sleeve sections being hingedly connected to said sleeve and rotatably outwardly therefrom when the cylinder of the syringe is received through said open sleeve end.

9. The combination needle sheath and sterility package recited in claim 8, further comprising means to surround said sleeve and thereby retain said sleeve sections in parallel alignment with one another, said surrounding and retaining means being removable from said sleeve to permit said sleeve sections to rotate away from one another when the syringe cylinder is received through the open end of said sleeve.

10. The combination needle sheath and sterility package recited in claim 9, wherein said surrounding and retaining means is a removable end cap to surround said sleeve and close the open end thereof.

11. The combination needle sheath and sterility package recited in claim 8, wherein the double ended needle cannula is supported by a hub that is adapted to be mated with the cylinder of the syringe so that the cannula can communicate with said cylinder, said hub including a base having adjacent side walls which are angled relative to one another, and said sleeve including a receptacle having adjacent side walls which are angled relative to one another to correspond with the angle of the side walls of said base, the base of said hub being received within the receptacle of said sleeve to align the needle cannula for communication with the syringe cylinder.

12. The combination needle sheath and sterility package recited in claim 11, further comprising at least one outwardly extending finger wing connected to said sleeve, the application of a rotational force to said finger wing being transferred to the base of said hub via the receptacle of said sleeve to cause said hub to be rotated into mating engagement with the cylinder of the syringe.

13. The combination needle sheath and sterility package recited in claim 8, wherein said needle cover and said sleeve are integrally connected to one another to form a one-piece combination.

14. For a double ended needle cannula to be positioned to communicate fluidically with the cylinder of a hypodermic syringe, a combination needle sheath and sterility package comprising a needle cover to surround and protect the distal end of the double ended needle cannula and a sleeve to surround and protect the proximal end of the cannula, said sleeve having an open end through which a portion of the syringe cylinder can be recieved so that the needle cannula can be positioned to communicate fluidically with the cylinder while the proximal end of the cannula is surrounded and protected by said sleeve, said sleeve also including expansible means being compressible from an expanded condition at which to surround and shield the proximal end of the needle cannula to a collapsed condition at which to permit said proximal end to communicate with the cylinder of the syringe when said cylinder is received through the open end of said sleeve.

15. The combination needle sheath and sterility package recited in claim 14, wherein said expansible means is a bellows.

16. The combination needle sheath and sterility package recited in claim 14, further comprising closure means removably attached across the open end of said sleeve.

17. The combination needle sheath and sterility package recited in claim 16, wherein said closure means comprises an end cap to cover the open end of said sleeve through which the syringe cylinder is to be received, said end cap being hingedly connected to said sleeve and rotatable from a position covering said sleeve to a position opening said sleeve for receipt of the cylinder.

18. The combination needle sheath and sterility package recited in claim 14, wherein the double ended needle cannula is supported by a hub that is adapted to be mated to the cylinder of the syringe so that the cannula can communicate with said cylinder, said hub including a base having adjacent side walls which are angled relative to one another, and said sleeve including a receptacle having adjacent side walls which are angled relative to one another to correspond with the angle of the side walls of said base, the base of said hub being received within the receptacle of said sleeve to align the needle cannula for communication with the syringe cylinder.

19. The combination needle sheath and sterility package recited in claim 18, further comprising at least one outwardly extending finger wing connected to said sleeve, the application of a rotational force to said finger wing being transferred to the base of said hub via the receptacle of said sleeve to cause said hub to be rotated into mating engagement with the cylinder of the syringe.

20. The combination needle sheath and sterility package recited in claim 14, wherein said needle cover and said sleeve are integrally connected to one another to form a one-piece combination.

* * * * *